(12) United States Patent
Agano

(10) Patent No.: US 7,209,142 B1
(45) Date of Patent: Apr. 24, 2007

(54) IMAGE DISPLAY METHOD AND AN IMAGE DISPLAY APPARATUS FOR IMPLEMENTING THE METHOD

(75) Inventor: Toshitaka Agano, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 794 days.

(21) Appl. No.: 09/617,308

(22) Filed: Jul. 14, 2000

(30) Foreign Application Priority Data

Jul. 15, 1999 (JP) .................................. 11-201667

(51) Int. Cl.
G09G 5/02 (2006.01)

(52) U.S. Cl. ........................................ 345/589; 345/605

(58) Field of Classification Search ................. 345/89, 345/90, 84, 99, 88, 589, 593, 597, 634, 691, 345/596, 605; 348/34, 694; 358/518, 520, 358/521, 517, 515
See application file for complete search history.

(56) References Cited

U.S. PATENT DOCUMENTS

| | | | | | |
|---|---|---|---|---|---|
| 5,122,872 | A | * | 6/1992 | Nagano | 358/524 |
| 5,185,712 | A | * | 2/1993 | Sato et al. | 348/333.08 |
| 5,210,600 | A | * | 5/1993 | Hirata | 358/76 |
| 5,414,529 | A | * | 5/1995 | Terada et al. | 358/448 |
| 5,654,756 | A | * | 8/1997 | Takahashi et al. | 348/268 |
| 5,721,578 | A | * | 2/1998 | Nakai et al. | 347/183 |
| 5,801,745 | A | * | 9/1998 | Wada et al. | 347/232 |
| 5,805,196 | A | * | 9/1998 | Nakanishi et al. | 347/230 |
| 5,926,292 | A | * | 7/1999 | Ishikawa et al. | 358/534 |
| 5,973,802 | A | * | 10/1999 | Hirota et al. | 358/521 |
| 6,002,459 | A | * | 12/1999 | Kaise et al. | 349/95 |
| 6,166,800 | A | * | 12/2000 | Silverstein et al. | 349/201 |
| 6,185,367 | B1 | * | 2/2001 | Keery et al. | 386/122 |
| 6,262,786 | B1 | * | 7/2001 | Perlo et al. | 349/95 |
| 6,285,800 | B1 | * | 9/2001 | Yamazaki et al. | 382/266 |
| 6,317,220 | B1 | * | 11/2001 | Fujita et al. | 358/1.9 |
| 6,317,521 | B1 | * | 11/2001 | Gallagher et al. | 382/260 |
| 6,342,896 | B1 | * | 1/2002 | Shetter et al. | 345/589 |
| 6,370,278 | B1 | * | 4/2002 | Waguri | 382/266 |
| 6,392,690 | B1 | * | 5/2002 | Fujii et al. | 348/59 |
| 6,570,613 | B1 | * | 5/2003 | Howell | 348/219.1 |
| 6,608,927 | B2 | * | 8/2003 | Ohta | 382/167 |
| 6,678,078 | B1 | * | 1/2004 | Popovich et al. | 359/15 |
| 6,714,208 | B1 | | 3/2004 | Yamaguchi | |

FOREIGN PATENT DOCUMENTS

| JP | 04-068391 | * 3/1992 |
|---|---|---|
| JP | 2000-330530 A | 11/2000 |

* cited by examiner

*Primary Examiner*—Richard Hjerpe
*Assistant Examiner*—Abbas Abdulselam
(74) *Attorney, Agent, or Firm*—Sughrue Mion, PLLC (57) ABSTRACT

The image display method and apparatus display a monochromatic image with a color display device in which a unit pixel is composed of R, G and B cells and display the monochromatic image having a higher gradation resolution than reproduction performance of each of the R, G and B cells in the color display device. In the method and apparatus, input data of the monochromatic image to be displayed on the color display device is allotted to R, G and B data for the R, G and B cells, respectively and the R, G and B data of the monochromatic image obtained by allotment is output to the R, G and B cells for display on the color display device. The method and apparatus can display an increased number of gradations so that monochromatic images used in the medical field can be displayed in a sufficiently high definition to suit diagnostic purposes.

27 Claims, 5 Drawing Sheets

12 LIQUID-CRYSTAL PANEL

FIG. 2B

UNIT PIXEL P

IMAGE DISPLAY METHOD AND AN IMAGE DISPLAY APPARATUS FOR IMPLEMENTING THE METHOD

BACKGROUND OF THE INVENTION

This invention relates to an image display method and an image display apparatus for implementing the method. More particularly, the invention relates to an image display method that can display an increased number of gradations or allows for enhanced reproduction of monochromatic image being displayed with a color display device in which a unit pixel consists of R, G and B cells. The invention also relates to an image display device for implementing the method.

The diagnostic images taken with medical diagnostic apparatus such as X-ray diagnostic apparatus, MRI (magnetic resonance imaging) apparatus and various types of CT (computed tomographic) apparatus are usually recorded on light-transmitting image recording films such as X-ray films and light-sensitive materials in film form and thereafter reproduced as light-transmissive images. The films showing the reproduced diagnostic images are set on a viewing device such as a so-called "Shaukasten", a light box and a transilluminator and illuminated with backlight so that the images are viewed for diagnosis.

Conventionally, apparatus for medical diagnosis and measurement have a CRT (cathode-ray tube) display or LCD (liquid-crystal display) connected as a monitor for viewing the images taken and measured with such apparatus. Diagnosis is performed on the basis of the image output to the monitor or the diagnostic images yet to be output on films are checked, adjusted or otherwise processed on the monitor.

The images taken with the medical diagnostic apparatus or those taken and measured with the apparatus for medical diagnosis and measurement are often reproduced on so-called "blue based" monochromatic films. The gradation resolution of the reproduced images is typically in 10 bits (providing 1024 gradations).

One problem is posed here. It is associated with the fact that CRTs usually display images at a gradation resolution of 8 bits and LCDs usually display images at a gradation resolution of 6 bits, sometimes in 8 bits if they are of the latest high-performance model. Thus, whichever of the monitors in current use display images with data having a lower gradation resolution than the image data that has been output after image taking and measurement with the above-described apparatus for medical diagnosis and measurement, that is to say, so-called "image data that cancellation of significant bits has occurred". Therefore, this "cancellation of the significant bits of the image data" occasionally causes a kind of noise called "artefacts" in contour lines which are commonly called pseudo-contours. Such noise will reduce or spoil the reliability of diagnoses and must be eliminated from medical diagnostic images.

To deal with this problem, it has been proposed to use a display technique by time division (for example, frame rate control which is hereunder abbreviated as FRC). In this technique, 10-bit image data may be divided by four to give four frames of 8-bit image data which are displayed consecutively in increasing frequency to represent a 10-bit gradation in 8 bits. However, this approach suffers from the problem of flicker in the image for the very reason that FRC is performed.

In order to eliminate flicker, the frame frequency in FRC display has to be increased to permit high enough display switching. In practice, however, the driver IC for the monitor and the monitor itself are limited in response speed. This problem presents considerable difficulty in medical diagnostic applications where an increased number of pixels are used with a view to providing higher image quality by representation of a high-definition image such as QSXGA (2560×2048 pixels).

SUMMARY OF THE INVENTION

The present invention has been accomplished under these circumstances and has as an object providing an image display method that solves the aforementioned problems with the prior art technology by displaying an increased number of gradations so that monochromatic images used in the medical field can be displayed in a sufficiently high definition to suit diagnostic purposes.

Another object of the invention is to provide an image display apparatus for implementing the method.

A further object of the invention is to provide an image display method that can display an increased number of gradations such that monochromatic images used in the medical field can be displayed as high-definition images that can be handled without presenting any unnatural feeling different from the images on the conventional "blue-based" monochromatic films doctors have gotten used to looking at for diagnostic purposes.

Yet another object of the invention is to provide an image display apparatus for implementing the method.

In order to attain the object described above, the first aspect of the present invention provides an image display method for displaying a monochromatic image with a color display device in which a unit pixel is composed of R, G and B cells, comprising the step of displaying the monochromatic image having a higher gradation resolution than reproduction performance of each of the R, G and B cells in the color display device.

Preferably, one pixel of the monochromatic image is displayed using the unit pixel composed of the R, G and B cells.

Preferably, input data of the one pixel of the monochromatic image is allotted to the R, G and B cells of the unit pixel.

Preferably, a minimum value and a maximum value of the input data are respectively allowed to correspond to approximate minimum and maximum luminance values as obtained by combining the R, G and B cells.

Preferably, the maximum value of the input data is converted to a sum of values for R, G and B cells and used as a new set of input data.

Preferably, data for each of the R, G and B cells in the input data has been obtained by generally equal allotment.

Preferably, data for each of the R, G and B cells in the input data, if expressed by coordinates (x,y) on a CIE chromaticity diagram, is within a region bounded by coordinates (0.174, 0.0), (0.4, 0.4) and ($\alpha$, 0.4) (where $\alpha$ is an x-coordinate of a point at which a spectrum locus crosses a straight line that is parallel to an x-axis and which intercepts a y-axis at 0.4).

Preferably, the input data and a mass of the data for each of R, G and B cells are used in 1:1 correspondence.

Preferably, data for each of the R, G and B cells is allotted to data for a plurality of time-divided frames and the data allotted to each of the time-divided frames is used to perform time-divided driving of the R, G and B cells independently of each other.

According to its second aspect, the present invention can be embodied as an image display apparatus for implementing the method according to its first aspect in order to attain the another object described above. To be more specific, the present invention can be embodied as an image display apparatus, comprising a color display device in which a unit pixel is composed of R, G and B cells, a data allotting unit by which input data of a monochromatic image to be displayed on the color display device is allotted to R, G and B data for the R, G and B cells, respectively, and a processing unit by which the R, G and B data of the monochromatic image obtained by allotment by the data allotting unit is output to the R, G and B cells for display on the color display device.

Preferably, the data allotting unit allows a minimum value and a maximum value of the input data to correspond respectively to approximate minimum and maximum luminance values as obtained by combining the R, G and B cells.

Preferably, the data allotting unit converts the maximum value of the input data to become equal to a sum of values for R, G and B cells.

Preferably, data for each of the R, G and B cells in the input data has been obtained by generally equal allotment.

Preferably, the data for each of the R, G and B cells in the input data, if expressed by coordinates (x,y) on a CIE chromaticity diagram, is within a region bounded by coordinates (0.174, 0.0), (0.4, 0.4) and ($\alpha$, 0.4) (where $\alpha$ is an x-coordinate of a point at which a spectrum locus crosses a straight line that is parallel to an x-axis and which intercepts a y-axis at 0.4).

Preferably, the input data and a mass of the data for each of R, G and B cells are used in 1:1 correspondence.

It is preferable that the image display apparatus further comprises a control means for allotting data for each of the R, G and B cells to data for a plurality of time-divided frames and performing time-divided driving of the R, G and B cells independently of each other using the data allotted to each of the time-divided frames.

DETAILED DESCRIPTION OF THE INVENTION

On the pages that follow, the image display, method and apparatus of the present invention are described in detail with reference to the preferred embodiments shown in the accompanying drawings.

Figure 1:
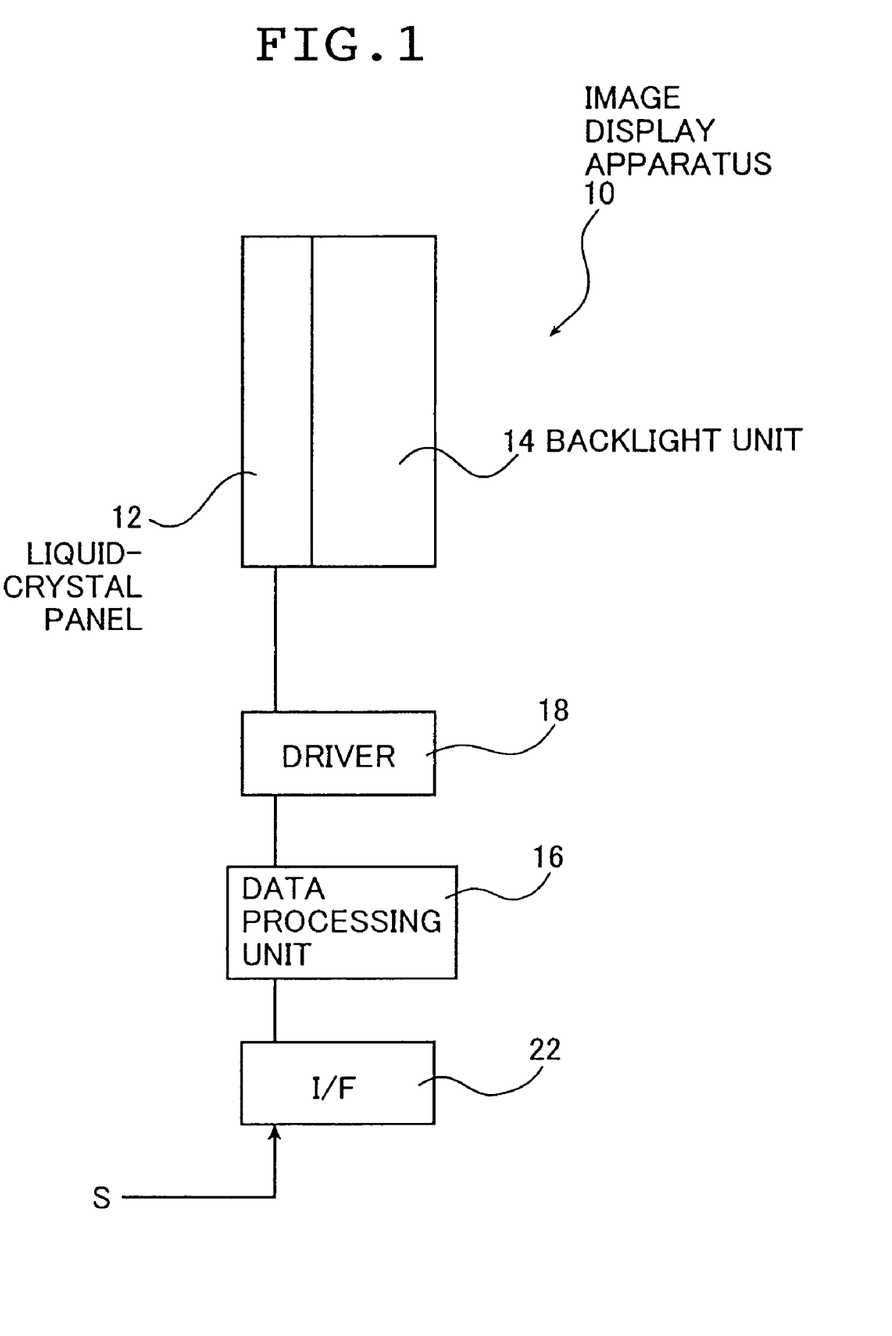
FIG. 1 shows in conceptual form an embodiment of the invention in which the claimed image display apparatus is used as a monitor for a medical diagnostic apparatus.

FIG. 1 shows in conceptual form an embodiment of the invention in which the claimed image display apparatus is used as a monitor for a medical diagnostic apparatus. The image display apparatus generally indicated by 10 in FIG. 1 is a liquid-crystal display (LCD) and comprises a color liquid-crystal panel 12 that displays images by liquid crystal, a backlight unit 14, a data processing unit 16 which performs data processing in the manner to be described later, a driver 18 of the color liquid-crystal panel 12, and an interface (I/F) 22.

The illustrated image display apparatus 10 is connected via the interface 22 to the image shooting or recording section S of medical diagnostic apparatus such as an X-ray diagnostic apparatus, an MRI diagnostic apparatus and various types of CT apparatus that are sources of diagnostic images to be displayed and from which image data are supplied to the image display apparatus 10.

In the LCD that can be used as the image display apparatus of the invention, the color liquid-crystal panel 12 is not limited to any particular type and all known color liquid-crystal panels that are used in various kinds of LCDs may be employed. The liquid-crystal panel 12 can be operated in all known modes including a TN (twisted nematic) mode, a STN (supertwisted nematic) mode and a MVA (multi-domain vertical alignment) mode.

The backlight unit 14 issues backlight for viewing the image displayed on the color liquid-crystal panel 12 and may have the same construction as the backlight mechanism in known LCDs. It should be noted that the image display apparatus 10 preferably has the ability to provide a display at a maximum luminance (brightness) of 500 cd/m$^2$ –5,000 cd/m$^2$ so that it can advantageously be used as a monitor in medical applications.

We now describe the functions of the data processing unit 16. The data processing unit 16 functions as the data allotting unit that is a characteristic part of the present invention and that allots the image data for the monochromatic image to be displayed on the liquid-crystal panel 12 to R (red), G (green) and B (blue) data, outputs the thus allotted R, G and B data for display to the driver 18 of the liquid-crystal panel 12. The data processing unit 16 further has the function such that for performing FRC display, the image data, for example, the 10-bit image data supplied from the image shooting section S is converted to the image data suitable for image display by the image display apparatus 10, for example, 8 bit image data and then supplied to the driver 18 of the liquid-crystal panel 12. In the description that follows hereinafter, the image data supplied from the image shooting section S is typically described as the 10-bit image data and the image data suitable for the image display is typically described as the 8-bit image data or the 10-bit image data. However, the present invention is by no means limited this sole case.

Figure 2A:
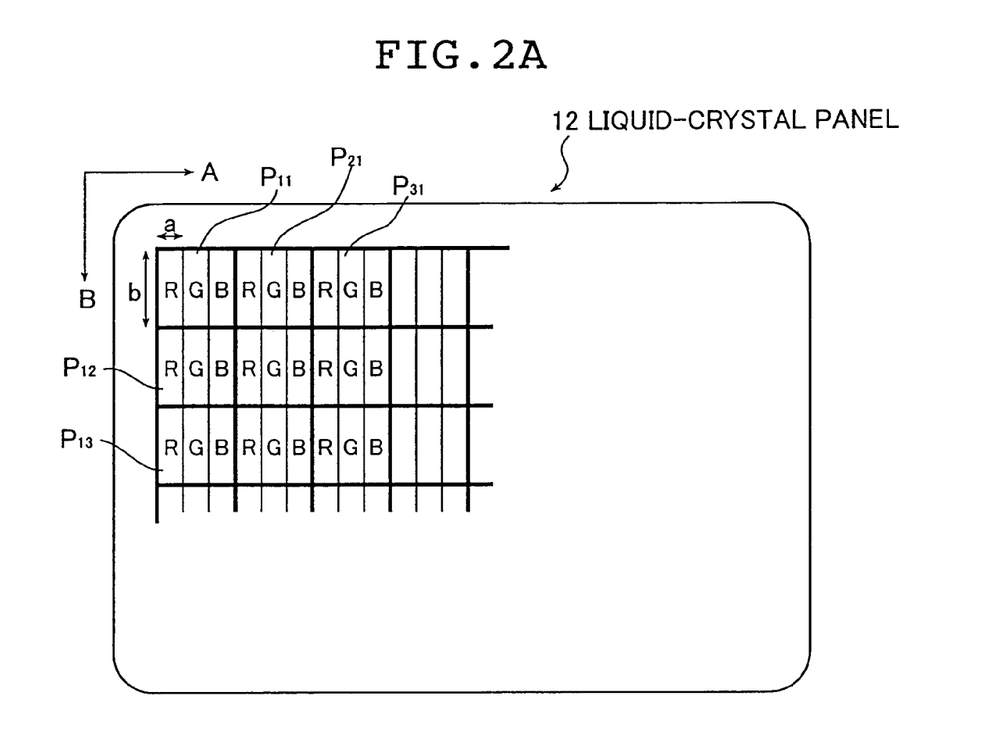
FIG. 2A is a partial enlarged view of the display screen of a color liquid-crystal display panel in the image display apparatus shown in FIG. 1.

FIG. 2A is a partial enlarged view of the display screen of the color liquid-crystal panel 12. As shown, the display screen of the color liquid-crystal panel 12 which is to be used with color filters contains ordered arrangements of R, G and B pixels in the horizontal direction (indicated by arrow A). Conventionally, such arrangements of R, G and B pixels are processed by the respective R, G and B image data to produce a color display. In the case under consideration, the same pixels are processed in the following special manner to display a high-definition monochromatic image.

The image display apparatus according to the embodiment under consideration displays a monochromatic image using unit pixels each consisting of the R, G and B pixels shown in FIG. 2A. Since each unit pixel is composed of R, G and B pixels for use with color filters, the luminance values that can be displayed with a single unit pixel are three times as many as those which can be displayed with each of the R, G and B pixels.

In other words, the interval between two luminance settings is divided by three to give a finer gradation to the displayed image. The image display apparatus according to the embodiment under consideration takes advantage of this effect and displays monochromatic images by ensuring that a minimum and a maximum value of image data respectively correspond to a minimum and a maximum gradation that can be displayed with each of the unit pixels defined above, namely, a minimum and a maximum luminance value in the color display of interest.

Figure 2B:
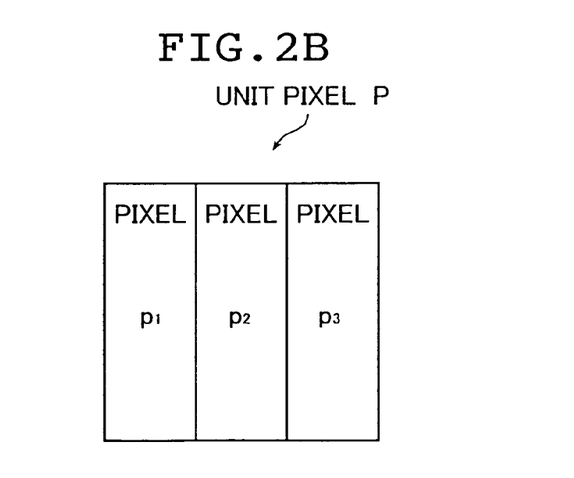
FIG. 2B shows three pixels constituting a unit pixel each assumed when displaying a monochromatic image.

Suppose here that each of the pixels p1, p2 and p3 shown in FIG. 2B performs 8-bit display. The luminance values that can be displayed range from 0 to 255 and those which can be displayed with a unit pixel P range from 0 to 765 (=255×3). In this case, the minimum luminance value zero is allowed to correspond to the minimum value (Min) of the image data and the maximum luminance value to the maximum value (Max) of the image data. This contributes to displaying an image of higher gradation. Another function of the data processing unit 16 is such that the luminance value converted from the image data is distributed substantially equally among the pixels p1, p2 and p2 when it is being supplied to the unit pixel P.

Figure 3:
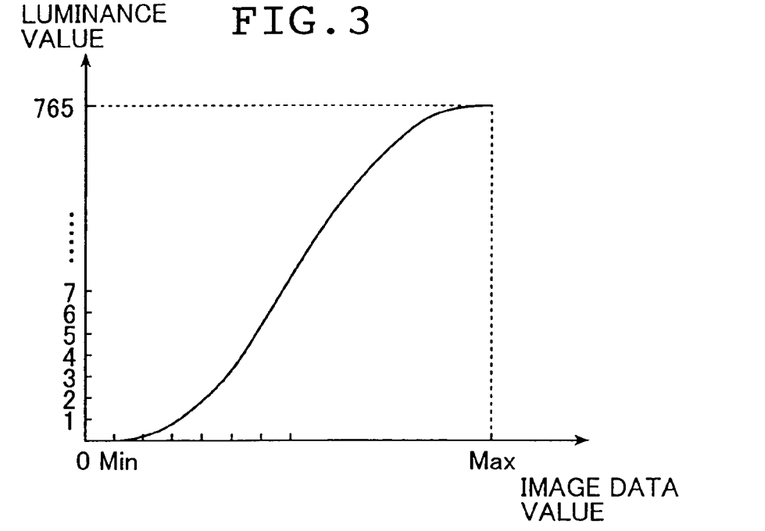
FIG. 3 is a graph showing an exemplary characteristic curve for relating an image data value to a luminance value.

To state more specifically, when 8-bit image data is input to the color display in which each of the pixels p1, p2 and p3 produces an 8-bit image, the minimum value (Min) of the image data which consists of values ranging from zero to 255 is allowed to correspond to the minimum luminance value zero on the color display and the maximum value (Max) of the image data to the maximum luminance value 765 on the same color display, with the intervening image data being converted to 765 levels of luminance by referring to the characteristic curve shown in FIG. 3 which relates an image data value to a luminance value.

In the next step, the luminance value converted from the image data is allotted to the pixels p1, p2 and p3 by the data processing unit 16 which distributes it substantially equally as shown in Table 1. Given the luminance value "0", the value zero is allotted to each of the pixels p1, p2 and p3. The luminance value "1" is allotted as 0, 1 and 0, the luminance value "2" as 1, 1 and 0, the luminance value "3" as 1, 1 and 1, the luminance value "4" as 2, 1 and 1, and so on until the luminance value "764" is allotted as 255, 255 and 254, and the final luminance value "765" as 255, 255 and 255. Thus, all luminance values converted from the image data are allotted to the individual pixels p1, p2 and p3 by substantially equal distribution.

TABLE 1

| Luminance value | Pixel p1 | Pixel p2 | Pixel p3 |
|---|---|---|---|
| 0 | 0 | 0 | 0 |
| 1 | 0 | 1 | 0 |
| 2 | 1 | 1 | 0 |
| 3 | 1 | 1 | 1 |
| 4 | 1 | 2 | 1 |
| . | . | . | . |
| . | . | . | . |
| . | . | . | . |
| 764 | 255 | 255 | 254 |
| 765 | 255 | 255 | 255 |

As described above, the luminance values are allotted by being distributed generally equally among the pixels p1, p2 and p3, so as to produce an image easy to look at, or a display that is characterized by the unit pixel P having less unevenness in brightness and which, therefore, presents less likelihood for physicians to make a wrong medical diagnosis. In the above explanation, the order of allotment is first to the pixel p2, then to p1 and finally to p3; however, this is not the sole example of luminance value allotment and other orders may of course be adopted.

Maximum values of monochromatic input image data will generally be in the range from about 255 (in 8 bits) to about 4095 (in 12 bits). Such input data is converted in the manner described above to produce new sets of input data which have maximum values in the range from 189 to 3069 as shown in Table 2 for the case where the FRC technique is not implemented. If the FRC technique is employed, the new sets of input data are as shown in Table 3.

TABLE 2

| | Without FRC |
|---|---|
| Input data | New sets of input data after conversion |
| 0–255 | 0–63 × 3 (= 189) |
| 0–511 | 0–127 × 3 (= 351) |
| 0–1023 → | 0–255 × 3 (= 765) |
| 0–2047 | 0–511 × 3 (= 1533) |
| 0–4095 | 0–1023 × 3 (= 3069) |

TABLE 3

| | With FRC |
|---|---|
| Input data | New sets of input data after conversion |
| 0–255 | 0–63 × 3 × 4 (= 756) |
| 0–511 | 0–127 × 3 × 4 (= 1524) |
| 0–1023 | 0–255 × 3 × 4 (= 3060) |
| . | . |
| . | . |
| . | . |

We now describe an example of the case in which the concept of the invention is applied to display monochromatic image as high-definition image that can be handled without presenting any unnatural feeling different from the images on the conventional "blue-based" monochromatic films doctors have got used to look at for diagnostic purposes. In this case, the data processing unit 16 allots data to R, G and B pixels that respectively correspond to the pixels p1, p2 and p3; an example of the allotment method for the case under consideration is shown in Table 4, in which the luminance values are allotted such that B data are provided with somewhat larger values than R and G data.

TABLE 4

| Luminance value | Pixel p1 | Pixel p2 | Pixel P3 |
|---|---|---|---|
| 0 | 0 | 0 | 0 |
| 1 | 0 | 0 | 1 |
| 2 | 0 | 1 | 1 |
| 3 | 1 | 1 | 1 |
| 4 | 1 | 1 | 2 |
| . | . | . | . |
| . | . | . | . |
| . | . | . | . |
| 764 | 244 | 244 | 254 |
| 765 | 245 | 245 | 255 |

To be more specific, the luminance values 0–765 are allotted such that B data has somewhat larger values than R and G data in the low-brightness area of the initial data but that the difference increases with increasing brightness. This is in order to ensure that if the same image is reproduced on a blue-based film, the low-density area (corresponding to the high-brightness area of the monitored image) has an intense blue shade whereas the high-density area (corresponding to the low-brightness area of the monitored image) has a weak blue shade, thus allowing the reproduced image to be viewed without suffering a drop in visual contrast.

As a result, the image on the color display can be viewed without presenting any unnatural feeling different from the image on conventional "blue-based" monochromatic films and yet featuring a higher definition.

Figure 4:
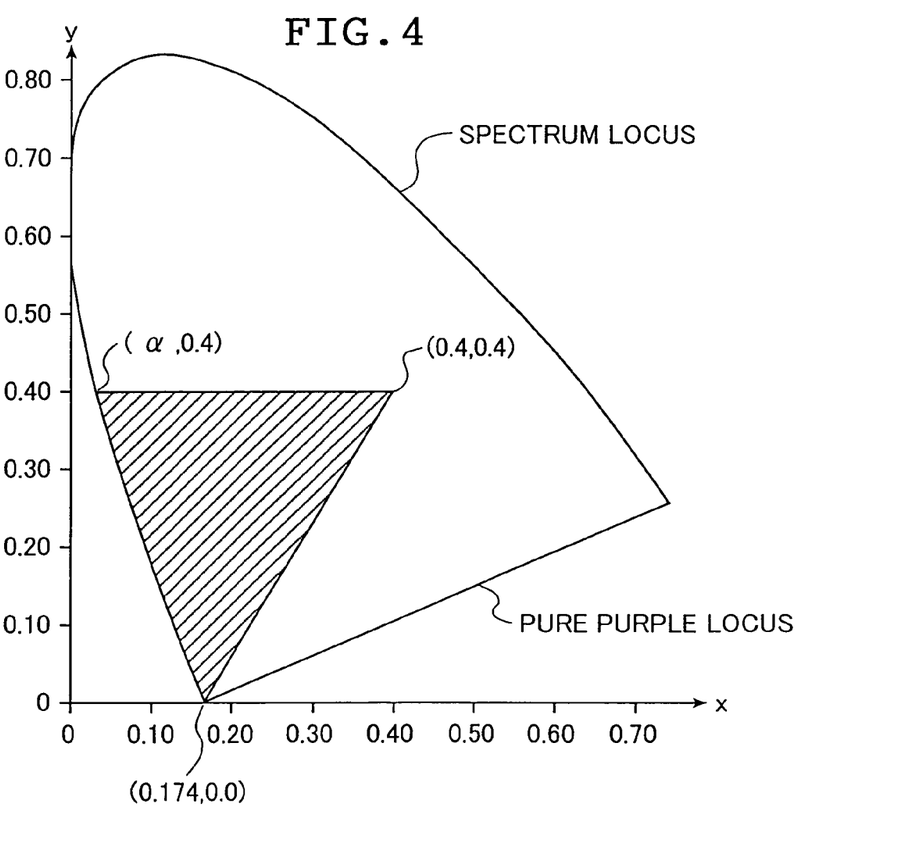
FIG. 4 is a diagram showing a preferred region of the chromaticity in which the image on a blue-based monochromatic film is to be reproduced by image processing in an embodiment of the invention.

Further referring to the allotment of RGB image data, the chromaticity of the image represented as the result of allotment is preferably within the hatched triangular region of the chromaticity diagram shown in FIG. 4 which is bounded by coordinates (0.174, 0.0), (0.4, 0.4) and ($\alpha$, 0.4) (where $\alpha$ is the x-coordinate of the point at which the spectrum locus crosses a straight line that is parallel to the x-axis and which intercepts the y-axis at 0.4). This corresponds to a visually preferred blue color.

As will be described below in detail, the function of the data processing unit 16 may be such that for performing FRC display, the 10-bit image data supplied from the image recording section S and obtained by above-described data allotment of the present invention is converted to 8-bit image data suitable for image display by the image display apparatus 10 and then supplied to the driver 18 of the liquid-crystal panel 12.

Figure 5:
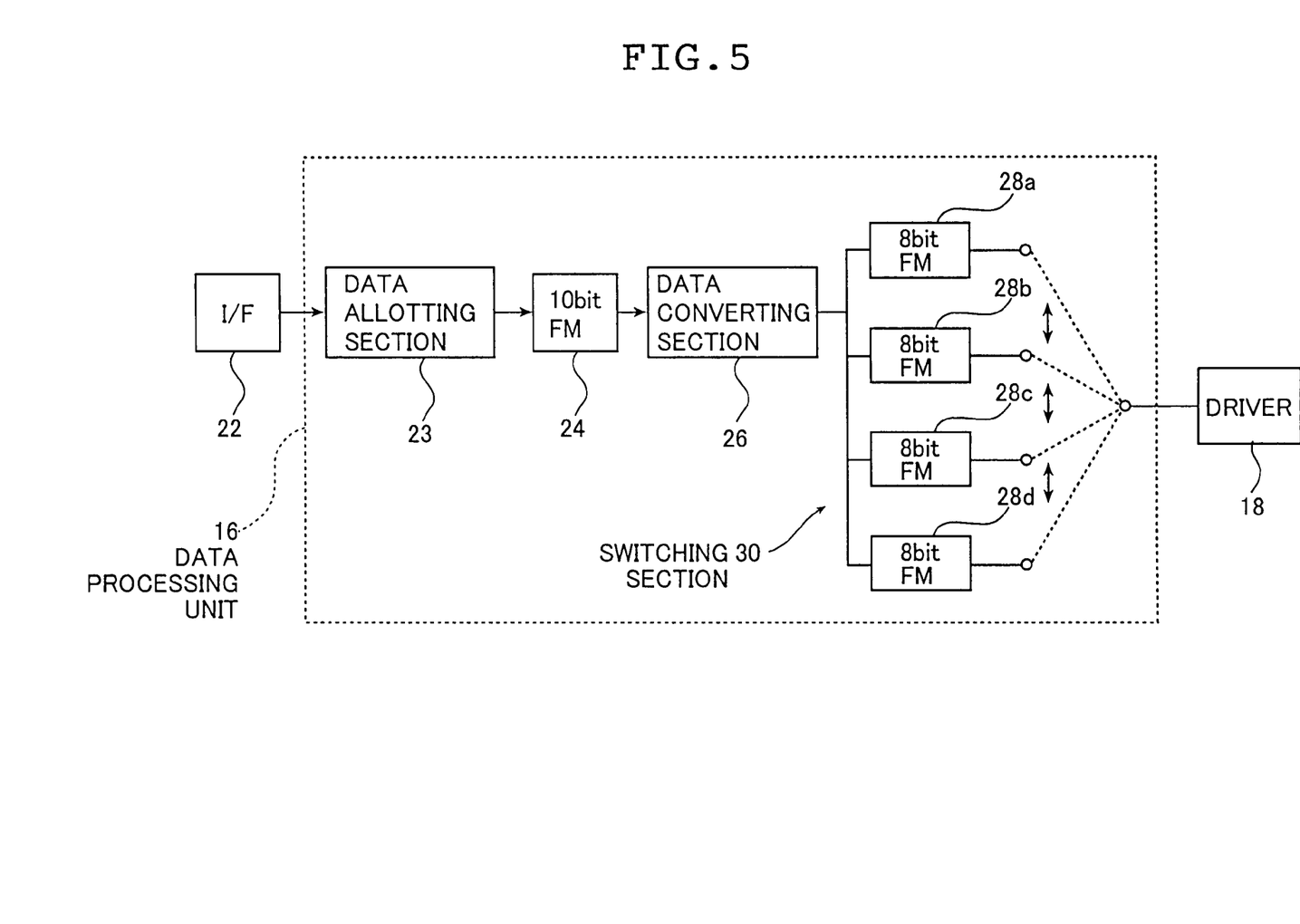
FIG. 5 is a block diagram for a data processing unit in the image display apparatus 10 shown in FIG. 1.

FIG. 5 is a block diagram for the data processing unit 16 having this function. As shown, the data processing unit 16 comprises a data allotting section 23 for performing the data allotment characterized by the present invention, a 10-bit frame memory 24, a data converting section 26, 8-bit frame memories 28a, 28b, 28c and 28d, and a switching section 30. The function of the switching section 30 is such that the 8-bit image data stored in the 8-bit frame memories 28a, 28b, 28c and 28d are sequentially output for FRC display.

In this data processing section 16, the 10-bit image data supplied from the interface 22 is allotted to R, G and B data as the 10-bit data in the data allotting section 23 and then 10-bit image data of each of R, G and B data is stored in the frame memory 24 and subsequently read into the data converting section 26, where it is converted to 8-bit image data.

Having this construction, the image display apparatus 10 in the embodiment under consideration can be operated in various ways. In one example, the aforementioned capability of FRC display is utilized to ensure that the image data having a gradation resolution of 10 bits as supplied from the image recording section S is processed by the image display apparatus 10 to permit image display as if the gradation resolution is the same (10 bits).

To this end, the initial 10-bit image data is displayed as an image consisting of 4 frames of 8-bit image data. The following is supplemental information about FRC display.

As is well known, FRC display is a technique for allowing image data of high bit number (high gradation resolution) to be displayed with image data of a lower bit number; to this end, the high-bit image data is processed to generate frames of lower-bit image data whose number depends on the difference in bit number, and the generated frames are successively displayed so that the display of a lower-bit image provides a gradation representation equivalent to the high bit number.

Specifically, if the difference in bit number is written as n, $2^n$ frames of image data with the lower bit number are generated and sequentially displayed. In this way, 4 frames of image data having a gradation resolution of 8 bits may be used to provide gradation representation equivalent to 10 bits, thereby enabling the display of an image which is very bright and yet does not have any artefacts.

As already mentioned, a display of 10-bit image can be represented by 4 frames of 8-bit image in FRC display.

In the embodiment under consideration, the data allotting section 23 of the data processing unit 16 makes allotment to RGB data in the manner described below. First, the initial RGB data consisting of 1024 pieces (0–1023) is allotted to R, G and G data, respectively, as shown in Table 5.

TABLE 5

| <Allotment to RGB data> | | | |
|---|---|---|---|
| Initial data | R data | G data | B data |
| 0 | 0 | 0 | 0 |
| 1 | 0 | 0 | 1 |
| 2 | 1 | 1 | 2 |
| 3 | 2 | 2 | 3 |
| 4 | 3 | 3 | 4 |
| 5 | 4 | 4 | 5 |
| 6 | 5 | 5 | 6 |
| 7 | 6 | 6 | 7 |
| 8 | 7 | 7 | 8 |
| 9 | 8 | 8 | 9 |
| 10 | 9 | 9 | 10 |
| 11 | 9 | 9 | 11 |
| 12 | 10 | 10 | 12 |
| . | . | . | . |
| . | . | . | . |
| . | . | . | . |
| 509 | 458 | 458 | 509 |
| 510 | 459 | 459 | 510 |
| 511 | 459 | 459 | 511 |
| 512 | 460 | 460 | 512 |
| . | . | . | . |
| . | . | . | . |
| . | . | . | . |
| 1021 | 918 | 918 | 1021 |
| 1022 | 919 | 919 | 1022 |
| 1023 | 920 | 920 | 1023 |

The allotted data is further allotted to frame data #1–#4 as shown in Table 6.

TABLE 6

| <Allotment to frame data> | | | | |
|---|---|---|---|---|
| | | Frame data | | |
| RGB data | #1 | #2 | #3 | #4 |
| 0 | 0 | 0 | 0 | 0 |
| 1 | 1 | 0 | 0 | 0 |
| 2 | 1 | 0 | 1 | 0 |
| 3 | 1 | 1 | 1 | 0 |
| 4 | 1 | 1 | 1 | 1 |
| 5 | 2 | 1 | 1 | 1 |
| 6 | 2 | 1 | 2 | 1 |
| 7 | 2 | 2 | 2 | 1 |
| 8 | 2 | 2 | 2 | 2 |
| 9 | 3 | 2 | 2 | 2 |
| 10 | 3 | 2 | 3 | 2 |
| 11 | 3 | 3 | 3 | 2 |
| 12 | 3 | 3 | 3 | 3 |
| . | . | . | . | . |
| . | . | . | . | . |
| . | . | . | . | . |
| 508 | 127 | 127 | 127 | 127 |

TABLE 6-continued

<Allotment to frame data>

| RGB data | Frame data | | | |
|---|---|---|---|---|
|  | #1 | #2 | #3 | #4 |
| 509 | 128 | 127 | 127 | 127 |
| 510 | 128 | 127 | 128 | 127 |
| 511 | 128 | 128 | 128 | 127 |
| 512 | 128 | 128 | 128 | 128 |
| . | . | . | . | . |
| . | . | . | . | . |
| . | . | . | . | . |
| 1019 | 255 | 255 | 255 | 254 |
| 1020 | 255 | 255 | 255 | 255 |
| 1021 | 255 | 255 | 255 | 255 |
| 1022 | 255 | 255 | 255 | 255 |
| 1023 | 255 | 255 | 255 | 255 |

In Table 6, the RGB data obtained by allotment as shown in Table 5 is further allotted into data for a plurality of FRC frames by the following method.

Figure 6:
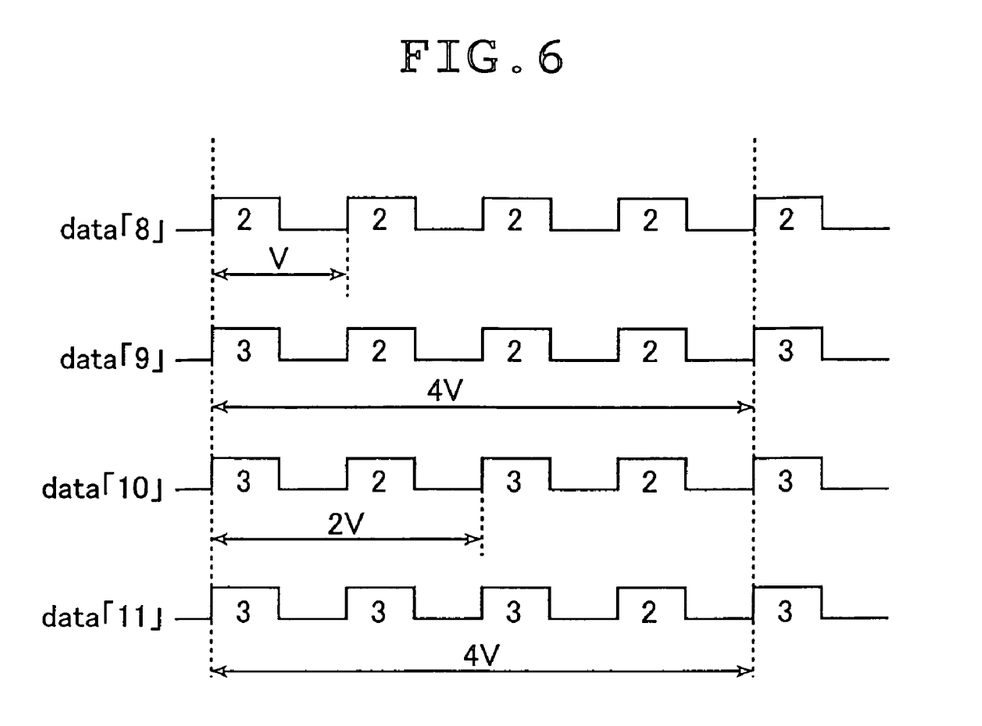
FIG. 6 is a timing chart for illustrating an example of image processing in the invention.

As already mentioned, a display of 10-bit image can be represented by 4 frames of 8-bit image data in FRC display. According to Table 6 and the timing chart in FIG. 6, 10-bit image data "8" is expressed by 8-bit image data in 4 frames consisting of 2, 2, 2 and 2. Similarly, 10-bit image data "9" is expressed by image data consisting of 3, 2, 2 and 2; 10-bit image data "10" by image data consisting of 3, 2, 3 and 2; and image data "11" by image data consisting of 3, 3, 3 and 2.

In the foregoing description of embodiments, the control of gradation display to be performed when monochromatic image is displayed using a color display device with unit pixels each consisting of R, G and B cells is accomplished either by the combination of area modulation and intensity modulation techniques in which the pixels are divided into a plurality of cells which are independently subjected to intensity modulation or by a time modulation technique typified by FRC. Needless to say, either method may be combined with time modulation by pulse width control or any other suitable technique of controlling gradation display.

It should also be noted that the foregoing embodiments are just two examples of the invention and are by no means intended to limit the present invention. An LCD is not the sole example of display devices that can be used in the invention and equally preferred results in display can be achieved with other kinds of display devices by performing the same control in accordance with the invention.

As described above in detail, the present invention ensures that the monochromatic image used in the medical field can be displayed as a high-definition image with a sufficient number of gradations to suit diagnostic purposes.

The invention also provides an image display apparatus that can advantageously be used in making such display.

As a further advantage, the image on the color display can be viewed without presenting any unnatural feeling different from the image on conventional "blue-based" monochromatic films and yet featuring a higher definition.

What is claimed is:

1. An image display method for displaying a monochromatic image of a predetermined color with a color display device in which a unit pixel is composed of R, G and B cells, comprising the steps of:

allotting a corresponding set of R, G and B data to each gradation of the monochromatic image having a larger number of gradations than a total number of gradations of the predetermined color that can be reproduced by each of the R, G and B cells in the color display device, by using sets of R, G and B data for the total number of gradations of the predetermined color and one or two sets of R, G and B data obtained by at least one of: changing only one of three R, G, B data input to the respective R, G and B cells and simultaneously changing only two of the three R, G and B data, when reproduction performance of each of the R, G and B cells in said color display device refers to the total number of gradations of the predetermined color represented by a total number of the sets of R, G and B data that are obtained by simultaneously changing by one the three R, G and B data input to the respective R, G and B cells in order to reproduce the predetermined color;

inputting the allotted corresponding set of R, G and B data to each of the R, G and B cells in said color display device; and displaying the monochromatic image having a higher gradation resolution than the reproduction performance of each of the R, G and B cells in said color display device.

2. The image display method according to claim 1, wherein one pixel of said monochromatic image is displayed using said unit pixel composed of said R, G and B cells.

3. The image display method according to claim 2, wherein input data of said one pixel of said monochromatic image is allotted to said R, G and B cells of said unit pixel.

4. The image display method according to claim 3, wherein a minimum value and a maximum value of said input data respectively correspond to approximate minimum and maximum luminance values as obtained by combining said R, G and B cells.

5. The image display method according to claim 4, wherein the maximum value of said input data is converted to a sum of values for R, G and B cells and used as a new set of input data.

6. The image display method according to claim 3, wherein data for each of the R, G and B cells in said input data has been obtained by generally equal allotment.

7. The method of claim 3, wherein data for each of the R, G and B cells in said input data, if expressed by coordinates (x, y) on a CIE chromaticity diagram, is within a region bounded by at least three coordinates.

8. The image display method according to claim 1, wherein data for each of said R, G and B cells is allotted to data for a plurality of time-divided frames and the data allotted to each of said time-divided frames is used to perform time-divided driving of said R, G and B cells independently of each other to produce said monochromatic image.

9. The method of claim 1, wherein said image data is based on an image being used for medical diagnosis.

10. The method of claim 1, wherein luminance values that are displayed with said unit pixel, are at least three times as many as those that are displayed with each of the R, G and B cells.

11. The method of claim 1, wherein the monochromatic image corresponds to a gradation resolution of N bits, and said each of the R, G, B cells corresponds to a gradation resolution corresponding to M bits, where N>M.

12. The method of claim 1, wherein said color display device is a liquid-crystal display device.

13. An image display method for displaying a monochromatic image with a color display device in which a unit pixel is composed of R, G and B cells, comprising the step of:

displaying the monochromatic image having a higher gradation resolution than reproduction performance of each of the R, G and B cells in said color display device, wherein one pixel of said monochromatic image is displayed using said unit pixel composed of said R, G and B cells, wherein input data of said one pixel of said monochromatic image is allotted to said R, G and B cells of said unit pixel, and wherein data for each of the R, G and B cells in said input data, if expressed by coordinates (x,y) on a CIE chromaticity diagram, is within a region bounded by coordinates (0.174,0.0), (0.4, 0.4) (where α is an x-coordinate of a point at which a spectrum locus crosses a straight line that is parallel to an x-axis and which intercepts a y-axis at 0.4).

14. The image display method according to claim 13, wherein said input data and a mass of the data for each of R, G and B cells are used in 1:1 correspondence.

15. An image display apparatus, comprising:
a color display device in which a unit pixel is composed of R, G and B cells;
a data allotting unit by which input data of a monochromatic image of a predetermined color to be displayed on said color display device is allotted to R, G and B data for the R, G and B cells, respectively; and
a processing unit by which the R, G and B data of the monochromatic image obtained by allotment by said data allotting unit, is output to the R, G and B cells for display on said color display device,
wherein said data allotting unit allots a corresponding set of R, G and B data to each gradation of the monochromatic image having a larger number of gradations than a total number of gradations of the predetermined color that can be reproduced by each of the R, G and B cells in the color display device, by using sets of R, G and B data for the total number of gradations of the predetermined color and one or two sets of R, G and B data obtained by at least one of: changing only one of the three R, G, B data input to the respective R, G and B cells and simultaneously changing only two of the three R, G and B data, when reproduction performance of each of the R, G and B cells in the color display device refers to the total number of gradations of the predetermined color represented by a total number of the sets of R, G and B data that are obtained by simultaneously changing by one the three R, G and B data input to the respective R, G and B cells in order to reproduce the predetermined color,
wherein said processing unit inputs the allotted corresponding set of R, G and B data to each of the R, G and B cells in said color display device, and
wherein said color display device displays the monochromatic image having a higher gradation resolution than the reproduction performance of each of the R, G and B cells in said color display device.

16. The image display apparatus according to claim 15, wherein said data allotting unit allows a minimum value and a maximum value of said input data to correspond respectively to approximate minimum and maximum luminance values as obtained by combining said R, G and B cells.

17. The image display apparatus according to claim 16, wherein said data allotting unit converts the maximum value of said input data to become equal to a sum of values for R, G and B cells.

18. The image display apparatus according to claim 15, wherein data for each of the R, G and B cells in said input data has been obtained by generally equal allotment.

19. The image display apparatus according to claim 15 further comprising a control means for allotting data for each of said R, G and B cells to data for a plurality of time-divided frames and performing time-divided driving of said R, G and B cells independently of each other using the data allotted to each of said time-divided frames to process said monochromatic image.

20. The apparatus of claim 15, wherein said input data is based on an image being used for medical diagnosis.

21. The apparatus of claim 15, wherein data for each of the R, G and B cells in said input data, if expressed by coordinates (x,y) on a CIE chromaticity diagram, is within a region bounded by at least three coordinates.

22. The apparatus of claim 15, wherein the monochromatic image corresponds to a gradation resolution of N bits, and said each of the R, G, B cells corresponds to a gradation resolution corresponding to M bits, where N>M.

23. The apparatus of claim 15, wherein said color display device is a liquid-crystal display device.

24. An image display apparatus, comprising:
a color display device in which a unit pixel is composed of R, G an B cells;
a data allotting unit by which input data of a monochromatic image to be displayed in said color display device is allotted to R, G and B data for the R, G and B cells, respectively; and
a processing unit by which the R, G and B data of the monochromatic image obtained by allotting unit is output to the R, G and B cells for display on said color display device,
wherein the monochromatic image is displayed having a higher gradation resolution than reproduction performance of each of the R, G and B cells in said color display device,
wherein data for each of the R, G and B cells in said input data, if expressed by coordinates (x, y) on a CIE chromaticity diagram, is within a region bounded by coordinates (0.174, 0.0), (0.4, 0.4) and (α is an x-coordinate of a point at which a spectrum locus crosses a straight line that is parallel to an x-axis and which intercepts a y-axis at 0.4).

25. The image display apparatus according to claim 24, wherein said input data and a mass of the data for each of R, G and B cells are used in 1:1 correspondence.

26. An image display apparatus, comprising:
a color display device in which a unit pixel is composed of R, G an B cells;
a data allotting unit by which input data of a monochromatic image to be displayed in said color display device is allotted to R, G and B data for the R, G and B cells, respectively; and
a processing unit by which the R, G and B data of the monochromatic image obtained by allotting unit is output to the R, G and B cells for display on said color display device,
wherein the monochromatic image is displayed having a higher gradation resolution than reproduction performance of each of the R, G and B cells in said color display device,
wherein said apparatus provides a display at a maximum luminance of approximately 500 cd/m$^2$–5000 cd/m$^2$.

27. An image display apparatus, comprising:

a color display device in which a unit pixel is composed of R, G an B cells;

a data allotting unit by which input data of a monochromatic image to be displayed in said color display device is allotted to R, G and B data for the R, G and B cells, respectively; and a processing unit by which the R, G and B data of the monochromatic image obtained by allotting unit is output to the R, G and B cells for display on said color display device, wherein the monochromatic image is displayed having a higher gradation resolution than reproduction performance of each of the R, G and B cells in said color display device, wherein said data allotting unit is in said processing unit, and said processing unit further comprises:

frame memories;

a data converting section; and a switching section for sequentially outputting data stored in said frame memories.

* * * * *